United States Patent
Wong

(10) Patent No.: US 10,501,537 B2
(45) Date of Patent: Dec. 10, 2019

(54) METHODS FOR TREATING CANCER

(71) Applicant: DANA-FARBER CANCER INSTITUTE, INC., Boston, MA (US)

(72) Inventor: Kwok-Kin Wong, Arlington, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/325,036

(22) PCT Filed: Jul. 7, 2015

(86) PCT No.: PCT/US2015/039379
§ 371 (c)(1),
(2) Date: Jan. 9, 2017

(87) PCT Pub. No.: WO2016/007513
PCT Pub. Date: Jan. 14, 2016

(65) Prior Publication Data
US 2017/0198039 A1    Jul. 13, 2017

Related U.S. Application Data

(60) Provisional application No. 62/026,992, filed on Jul. 21, 2014, provisional application No. 62/021,557, filed on Jul. 7, 2014.

(51) Int. Cl.
*C07K 16/28*   (2006.01)
*A61K 39/395*   (2006.01)
*A61K 31/506*   (2006.01)
*G01N 33/574*   (2006.01)
*A61K 39/00*   (2006.01)

(52) U.S. Cl.
CPC ........ *C07K 16/2803* (2013.01); *A61K 31/506* (2013.01); *A61K 39/39533* (2013.01); *C07K 16/2818* (2013.01); *G01N 33/574* (2013.01); *A61K 2039/507* (2013.01); *C07K 2317/31* (2013.01); *C07K 2317/76* (2013.01); *G01N 2333/70503* (2013.01)

(58) Field of Classification Search
CPC ........ C07K 16/00–468; C07K 16/2803; C07K 16/2818; A61K 39/395–39558
See application file for complete search history.

(56) References Cited

U.S. PATENT DOCUMENTS

2012/0094999 A1* 4/2012 Gray .................... C07D 473/16
                                                   514/235.8

FOREIGN PATENT DOCUMENTS

| CN | 103721255 A | 4/2014 |
| WO | WO 2011/159877 A2 | 12/2011 |
| WO | WO 2014/070874 A1 | 5/2014 |

OTHER PUBLICATIONS

Sakuishi et al., J. Exp. Med., 207(10): 2187-94 (Year: 2010).*
Reiss et al., Immunotherapy 6:459-475 (Year: 2014).*
Sakuma et al., Lab Invest. 92:371-83 (Year: 2012).*
Sakuishi, K. et al., "Targeting Tim-3 and PD-1 pathways to reverse T cell exhaustion and restore anti-tumor immunity," *Journal of Experimental Medicine* (2010) 207 (10): 2187-2194.
Akbay, E. A. et al. (2013) "Activation of the PD-1 pathway contributes to immune escape in EGFR-driven lung tumors" *Cancer Discov.*, 3:1355-63.
*Comprehensive Medicinal Chemistry*, (1992) C.A. Ramsden Gd., Chapter 17.2, F. Choplin Pergamon Press, 28 pages.
Goding, S. et al. (2013) "Restoring Immune Function of Tumor-Specific CD4+ T Cells During Recurrence of Melanoma" *J Immunol*, 190(9):4899-4909. NIH Public Access Author Manuscript, 22 pages.
Li, D. et al. (2007) "Bronchial and Peripheral Murine Lung Carcinomas Induced by T790M-L858R Mutant EGFR Respond to HKI-272 and Rapamycin Combination Therapy" *Cancer Cell*, 12:81-93.
Mansoori, B. et al. (2017) "The Different Mechanisms of Cancer Drug Resistance: A Brief Review" *Adv Pharm Bull*, 7(3):339-348.
Yoneda, A. et al. (2013) "T cell immunoglobulin domain and mucin domain-3 as an emerging target for immunotherapy in cancer management" *ImmunoTargets and Therapy*, 2:135-141.
Zhou, Q. et al. (2011) "Coexpression of Tim-3 and PD-1 identifies a CD8+ T-cell exhaustion phenotype in mice with disseminated acute myelogenous leukemia" *Blood*, 117(17):4501-4510.
Atezolizumab label, Initial US Approval 2016, revised Dec. 2018, 34 pages.
Avelumab label, Initial US Approval 2017, Revised Oct. 2018, 25 pages.
Durvalumab label, Initial US Approval 2017, Revised Feb. 2018, 27 pages.
Nivolumab label, Initial US Approval 2014, 89 pages.
Pembrolizumab label, Initial US Approval 2014, 64 pages.
Lee, A. et al., "Recent progress in therapeutic antibodies for cancer immunotherapy," Current Opinion in Chemical Biology, 44:56-65 (2018).
Oweida, A. et al., "Resistance to Radiotherapy and PD-L1 Blockade Is Mediated by TIM-3 Upregulation and Regulatory T-Cell Infiltration," Clin Cancer Res, 24(21):5368-5380 (2018).

\* cited by examiner

*Primary Examiner* — Jessica H Roark
(74) *Attorney, Agent, or Firm* — Cooley LLP; Cynthia A. Kozakiewicz; Ivor R. Elrifi

(57) ABSTRACT

The present invention provides methods of treating cancer, particularly cancers that had developed resistance to PD-1 and PDL-1 blockade. Also included are methods of identifying therapeutic targets for the treatment of cancer.

13 Claims, 15 Drawing Sheets

METHODS FOR TREATING CANCER

RELATED APPLICATIONS

This application is a US national stage application filed under 35 U.S.C. § 371 of PCT/US2015/039379 filed on Jul. 7, 2015 and claims priority to, and the benefit of, U.S. Provisional Application No. 62/021,557 filed on Jul. 7, 2014, U.S. Provisional Application No. 62/026,992 filed on Jul. 21, 2014, and the contents of each of which are incorporated herein by reference in their entireties.

FIELD OF THE INVENTION

The present invention relates generally to treating cancer. Also included are methods of identifying therapeutic targets for the treatment of cancer.

BACKGROUND OF THE INVENTION

The immune system must achieve a balance between effective responses to eliminate pathogenic entities and maintaining tolerance to prevent autoimmune disease. T cells are central to preserving this balance, and their proper regulation is primarily coordinated by the B7-CD28 family of molecules. Interactions between B7 family members, which function as ligands, and CD28 family members, which function as receptors, provide critical positive signals that not only initiate, augment and sustain T cell responses, but also contribute key negative signals that limit, terminate and/or attenuate T cell responses when appropriate. A member of the CD28 family, called PD-1 (also known as programmed cell death-1) is upregulated on activated T cells, B cells, and monocytes. PD-1 has two identified ligands in the B7 family, PD-L1 (also known as BH71 or programmed cell death-1 ligand 1) and PD-L2. While PD-L2 expression tends to be more restricted, found primarily on activated antigen-presenting cells (APCs), PD-L1 expression is more widespread, including cells of hematopoietic lineage (including activated T cells, B cells, monocytes, dendritic cells and macrophages) and peripheral nonlymphoid tissues (including heart, skeletal, muscle, placenta, lung, kidney and liver tissues).

More recently, it has been shown that some cancers have developed immune evasion tactics that specifically exploit the PD-1/PD-L1 axis by causing PD-1/PD-L1-mediated T cell exhaustion. Many human tumor cells and tumor-associated antigen presenting cells express high levels of PD-L1, which suggests that the tumors induce T cell exhaustion to evade anti-tumor immune responses. Agents that block the PD-1/PD-L1 pathway are new therapeutic targets for a variety of cancers. To date, PD-1/PD-L1 blockade has been successful in treating a number of cancers, however some patients receiving these treatments develop resistance to these treatments. Thus a need exists for methods to determine which patients are developing resistance to treatment as well as methods for overcoming the resistance.

SUMMARY OF THE INVENTION

The invention provides a method of treating or preventing PD-1 or PDL-1 resistance in a subject by administering to the subject a compound that inhibits the expression or activity of a T cell immunoglobulin and mucin protein 3 Tim3). The cancer is a KRAS or EGFR mutant cancer. For example, the cancer has an EGFR T90M L858R mutation. The cancer is a lung cancer, melanoma, kidney cancer, a head and neck cancer, bladder cancer or an upper gastrointestinal cancer. The kidney cancer is a renal cell cancer. The lung cancer is a non-small-cell lung cancer.

The compound is a nucleic acid, an antibody or a small molecule. Preferably, the compound is a bi-specific antibody. In some embodiments, the subject has received PD-1 or PDL-1 therapy. In other embodiments the subject is further administered PD-1 or PDL-1 therapy. The PD-1 or PDL-1 therapy is administered concurrently or sequentially with the Tim3 inhibitor.

The PD-1 or PDL-1 therapy is immunotherapy. In further embodiments, the subjects is further administered a chemotherapeutic agent or radiation therapy. For example, the chemotherapeutic agent is a targeted therapy. For example, the targeted therapy is a kinase inhibitor such as WZ4002.

Also included in the invention are methods of determining whether a subject has acquired PD-1 or PDL-1 resistance by detecting the expression level of Tim3 in a subject sample. An increase of expression of Tim3 compared to a normal control cell indicates that the subject has PD-1 or PDL-1 resistance.

Further included in the invention are methods of selecting a subject whom would derive a benefit from PD-1 or PDL-1 therapy, by detecting the expression level of Tim3 in a subject sample. A similarity of expression of Tim3 compared to a normal control cell indicates that the subject would derive a benefit from PD-1 or PDL-1 therapy. The normal control cell is T cells from cancer associated tissues that has not been exposed to PD-1 or PDL-1 blockade. For example, the T cells are derived from the subject before PD-1 or PDL-1 blockade.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

A) Schematic for the analysis of short-term treatment. Analysis of the expression of T cell checkpoint receptors in: B) CD4 T cells and C) CD8 T (cytotoxic) cells in EGFR T790M L858R mutant tumors either untreated or treated for 8 days with either irreversible EGFR tyrosine kinase inhibitor (WZ4002) or combination of WZ4002 and anti-PD1 antibody.

Figure 1:
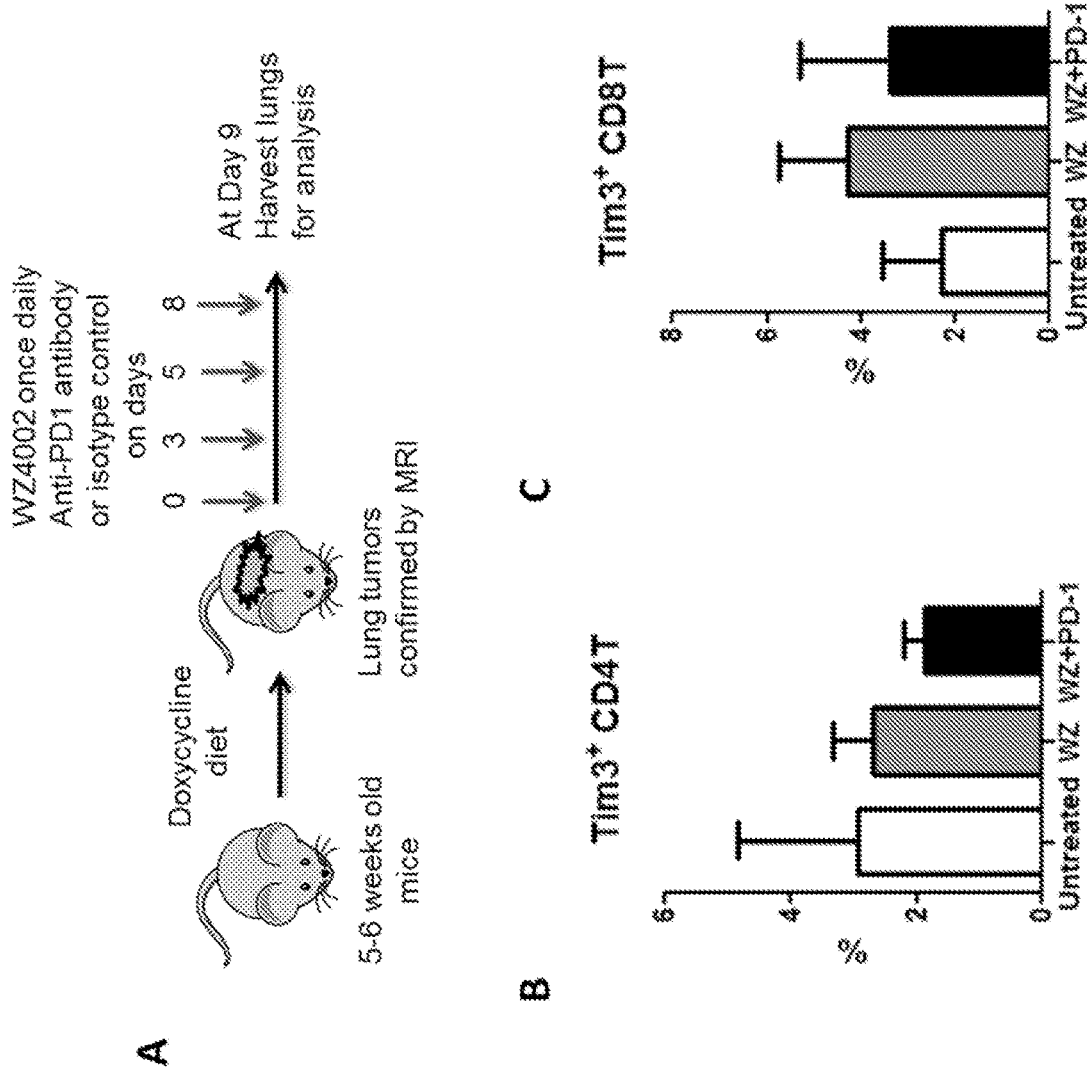
FIG. 1: Short-term treatment with anti-PD-1 antibody does not induce TIM3 expression in EGFR T790M L858R mutant mouse lung tumors.
Figure 2:
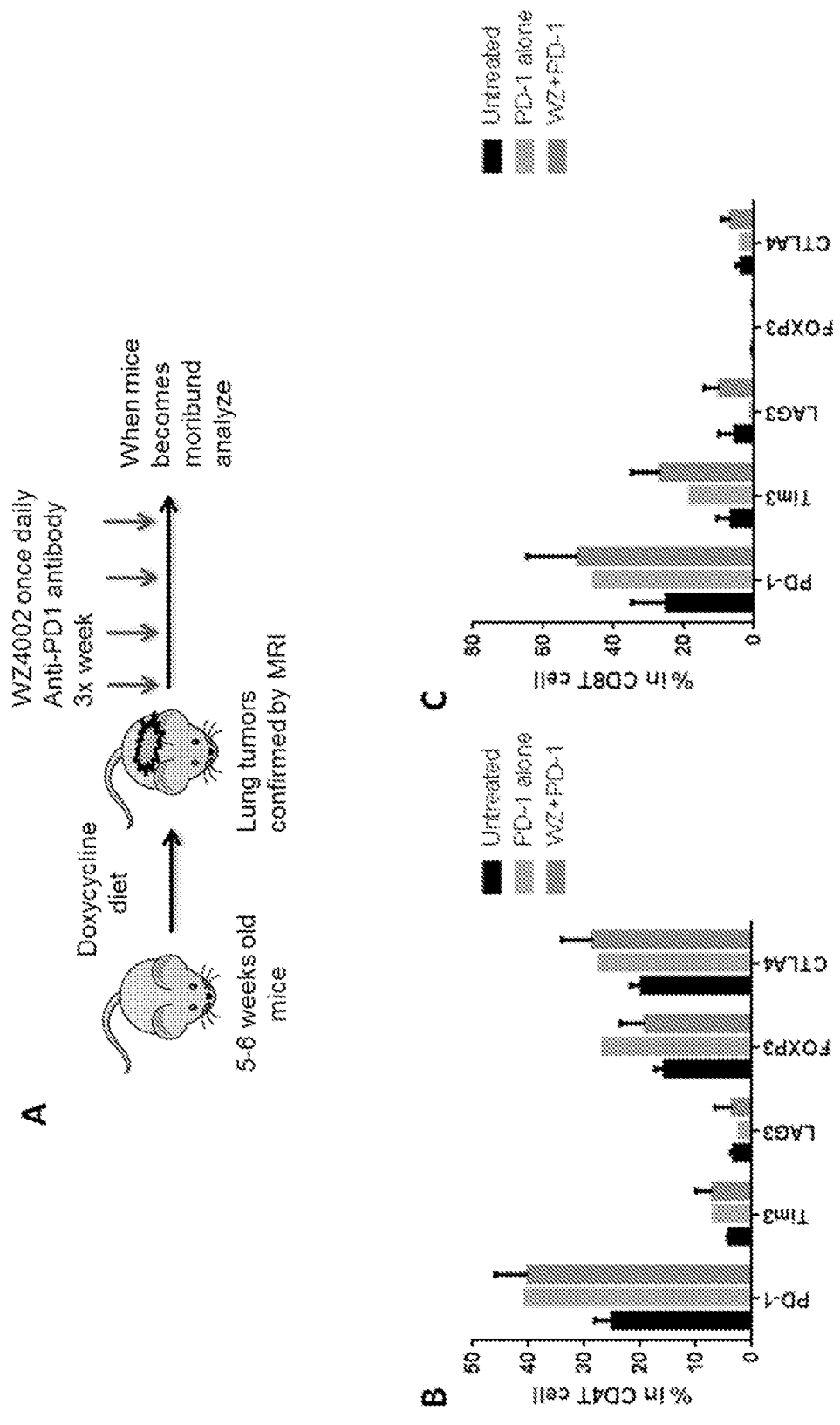

FIG. 2: Long term treatment with anti-PD-1 antibody or anti-PD-1 antibody in combination with EGFR TKI WZ4002 induces TIM3 expression A) Schematic for the analysis of long-term treatment. Mice were analyzed when they reached tumor burden euthanasia criteria. Analysis of the expression of T cell checkpoint receptors in: B) CD4 T cells and C) CD8 T cells in EGFR T790M L858R mutant tumors either untreated or treated with either WZ4002 or combination of WZ4002 and anti-PD1 antibody until they reach study endpoint.

Figure 3:
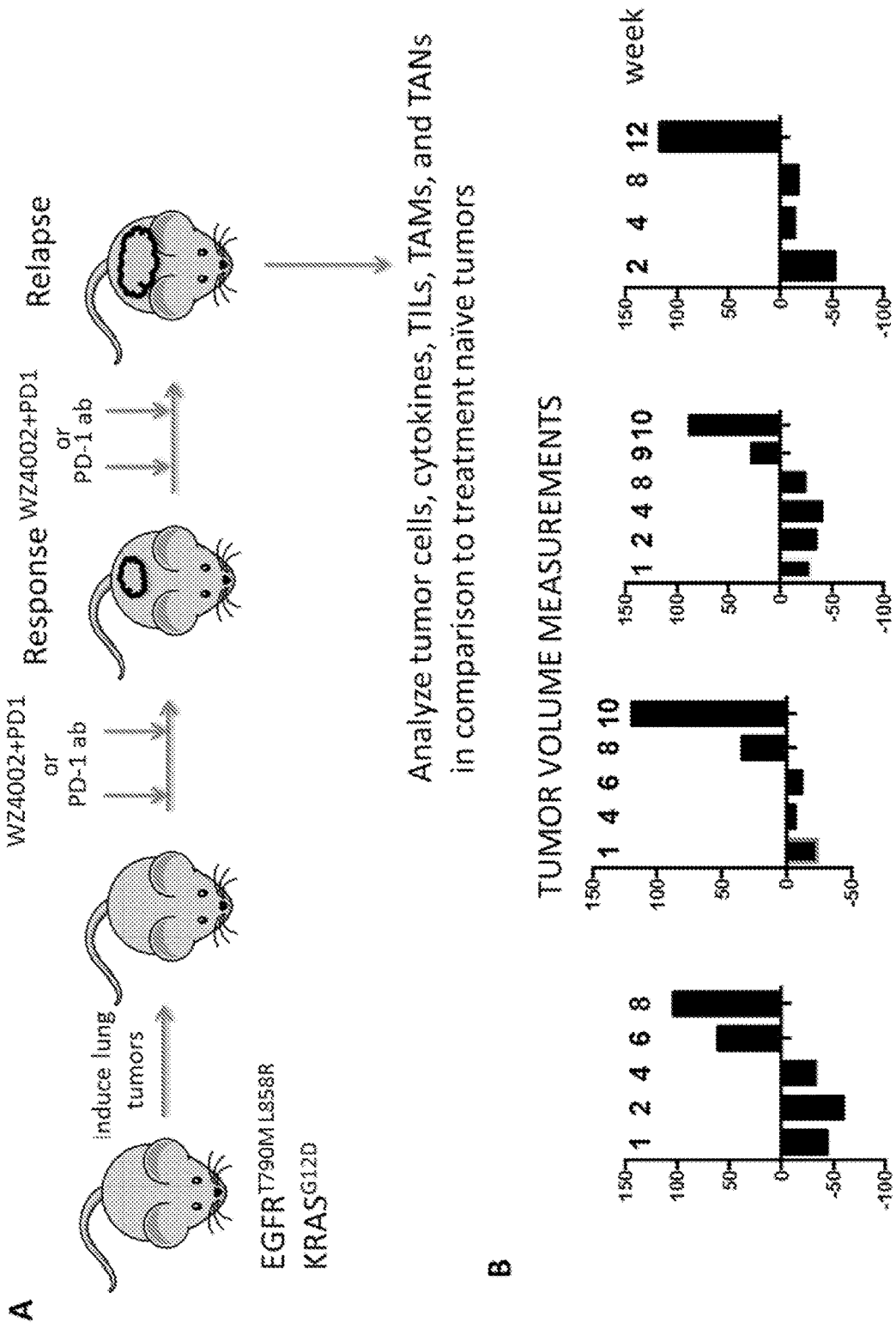

FIG. 3: Tumors develop resistance to PD-1 blockade treatment A) Schematic for the analysis of long-term treatment with either PD1 on EGFR or Kras models or WZ4002 and PD1 in EGFR mutant mouse model. B) Waterfall plots of lung tumor quantification using MR imaging during PD-1 blockade treatment.

Figure 4:
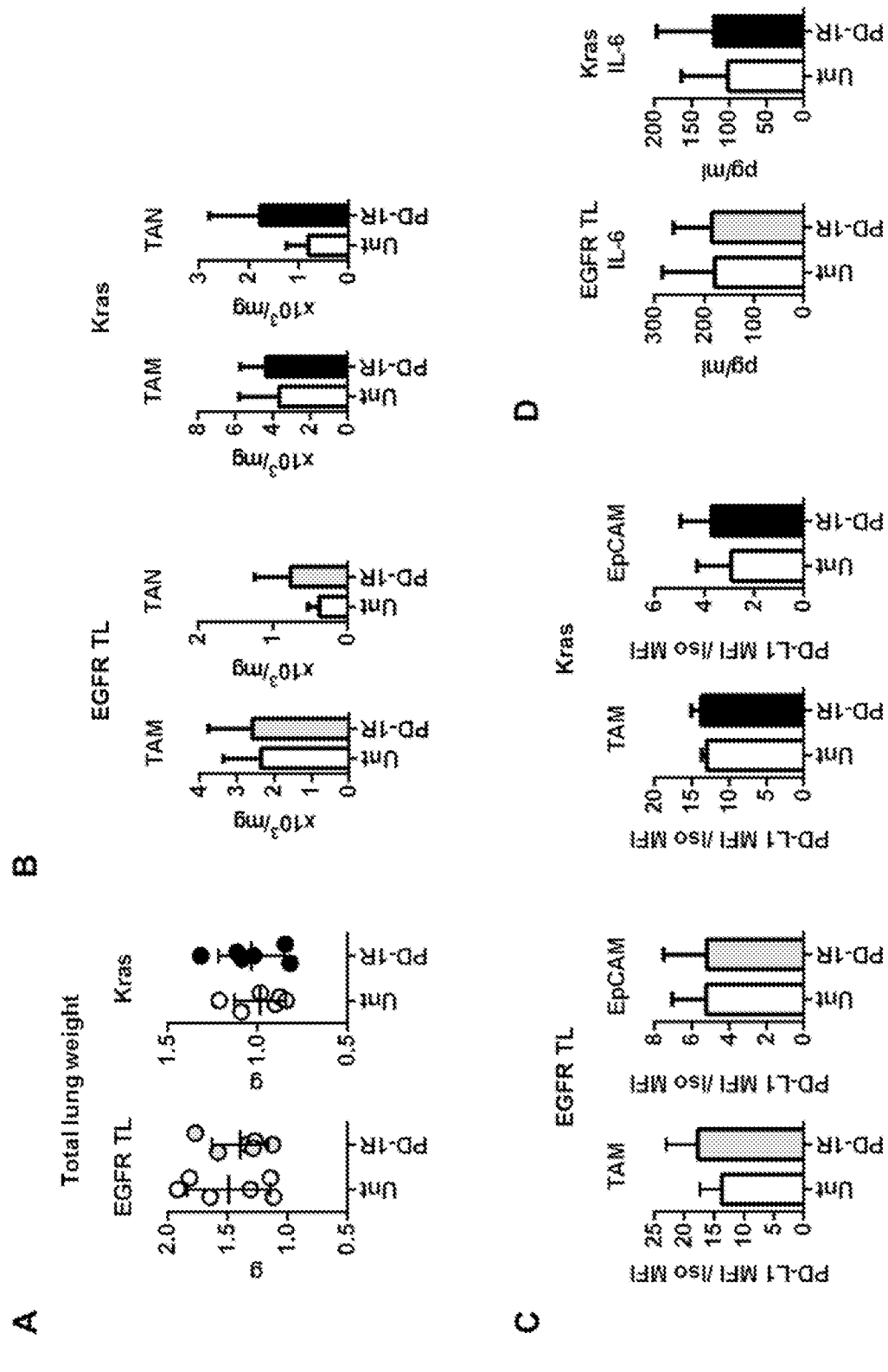

FIG. 4: Analysis of immune environment in PD-1 resistant EGFR and Kras mutant tumors A) Total lung weights showing tumor burden in the mice analyzed for these experiments. B) Total counts of myeloid cells; tumor associated macrophages and tumor associated neutrophils show no significant difference between naïve (unt) and PD-1 resistant tumors (PD-1). C) PD-L1 expression in myeloid cells and tumor cells, and D) Levels of proinflammatory cytokine IL-6 in naïve and treatment resistant tumors.

Figure 5:
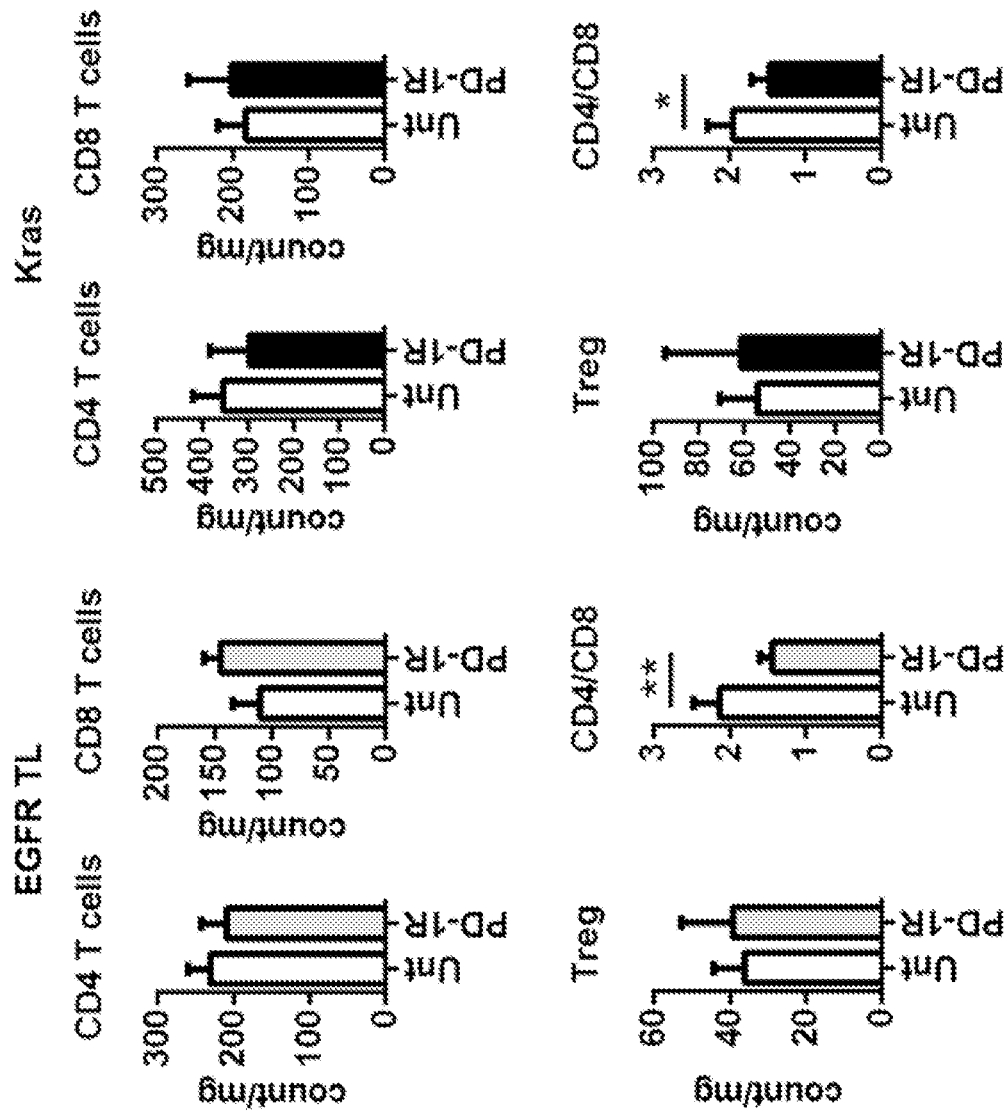

FIG. 5: Total counts of T cell subsets in PD-1 resistant EGFR and Kras mutant tumors Cell number of T cell subsets: CD4 T cells, CD8 T cells and regulatory T cells (Treg) and CD4/CD8 ratio. Untreated EGFR TL (n=6), Kras (n=6) and anti-PD-1 resistant (PD-1R) EGFR TL (n=6), Kras (n=6) were analyzed (EGFR TL **P=0.0013, Kras *P=0.0161).

Figure 6:
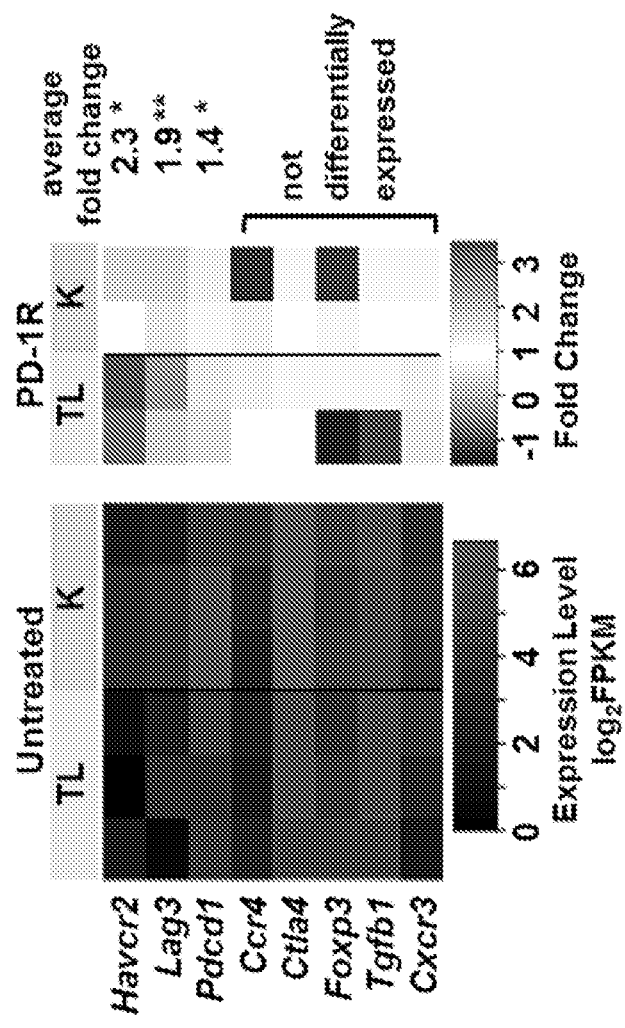

FIG. 6: RNA sequencing analysis of sorted T cells from PD-1 resistant EGFR and Kras mutant tumors Expression of 8 genes with an annotated role in the T cell response in sorted T cells from 4 anti-PD-1 treated and 6 untreated tumors in EGFR and Kras models. For each sample, the expression values across untreated samples are plotted as log-transformed FPKM values (colored black/red for low/high expression, respectively) and the fold change for resistant samples compared to genotype-matched untreated samples (colored blue/red for low/high fold change, respectively). Differentially expressed genes are shown with their average fold-change values across resistant tumors. One star indicates a q-value<0.1 in the EGFR model (Havcr2 and Pdcd1) and two stars in both the EGFR and Kras model (Lag3).

Figure 7:
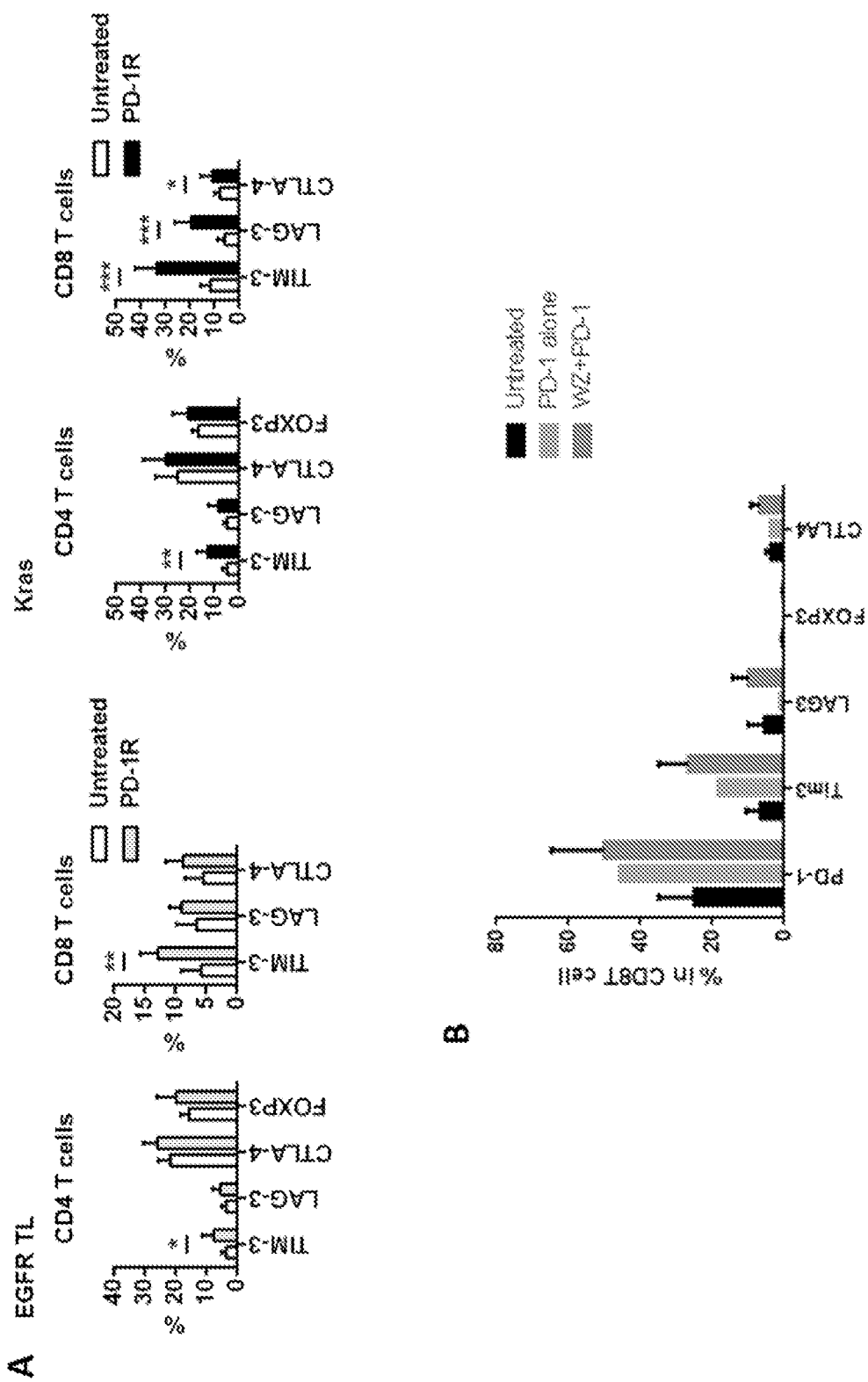

FIG. 7: Long term treatment with anti-PD-1 antibody or anti-PD-1 antibody in combination with EGFR TKI WZ4002 induces TIM3 expression A) Analysis of the expression of T cell checkpoint receptors in: CD4 T cells and CD8 T cells in both EGFR T790M L858R and Kras mutant mice treated long term with PD-1 blocking antibody and in B) EGFR T790M L858R mutant tumors either untreated or treated with either WZ4002 or combination of WZ4002 and anti-PD1 antibody until they reach study endpoint.

Figure 8:
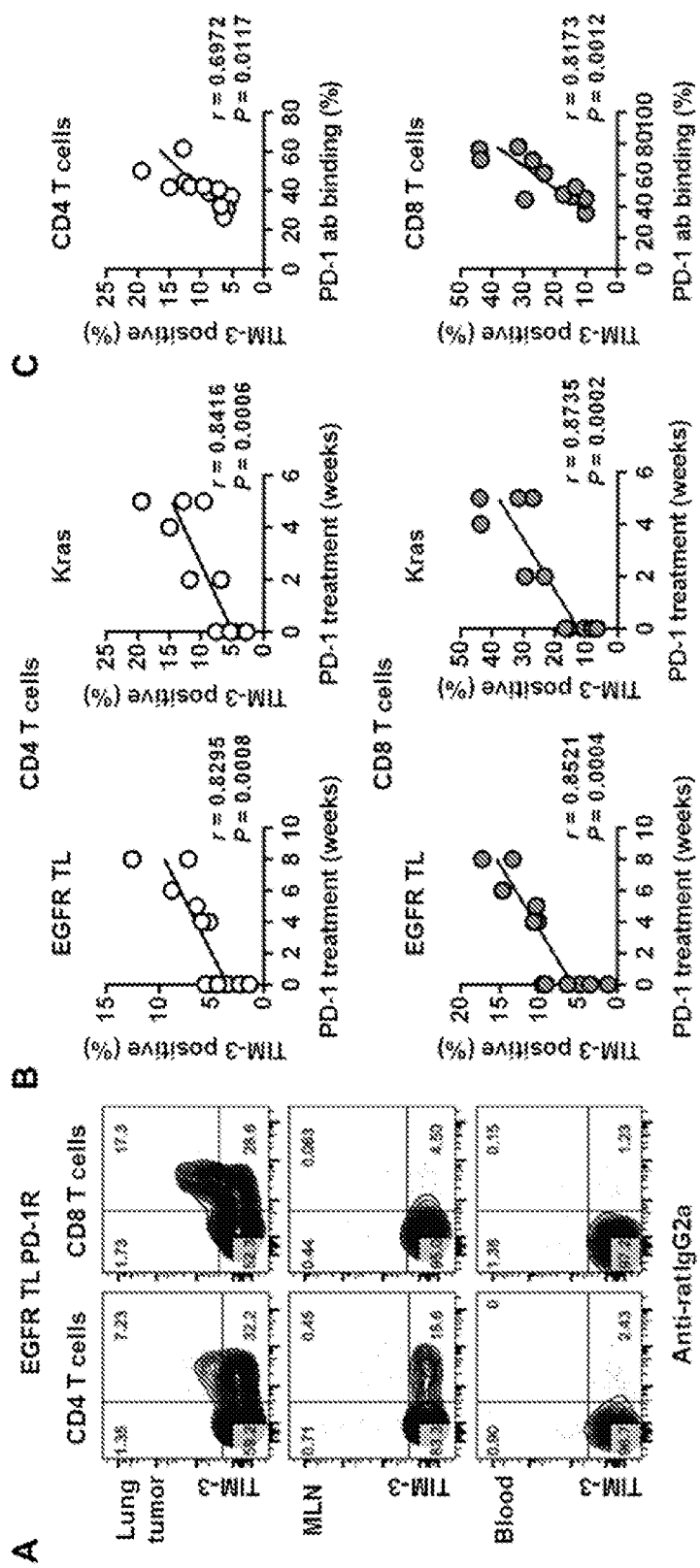

FIG. 8: TIM-3 upregulation is observed in therapeutic anti-PD-1 antibody bound tumor-infiltrating T cells and the level of expression is correlated with treatment length and anti-PD-1 antibody binding A) TIM-3 expression in T cells from tumor bearing lung, mediastinal lymph node and peripheral blood. Representative flow cytometry data from anti-PD-1 resistant (PD-1R) EGFR TL mouse. B) Significant correlation was detected between TIM-3 positivity and the duration of PD-1 blocking treatment in EGFR TL mice (untreated (0 week): n=6 and anti-PD-1 resistant: n=6) and Kras mice (untreated: n=6 and anti-PD-1 resistant: n=6). C) Significant correlation was detected among TIM-3 positivity and the amount of bound therapeutic PD-1 antibody in anti-PD-1 resistant EGFR TL and Kras mice (both EGFR and Kras mice were combined: n=12).

Figure 9:
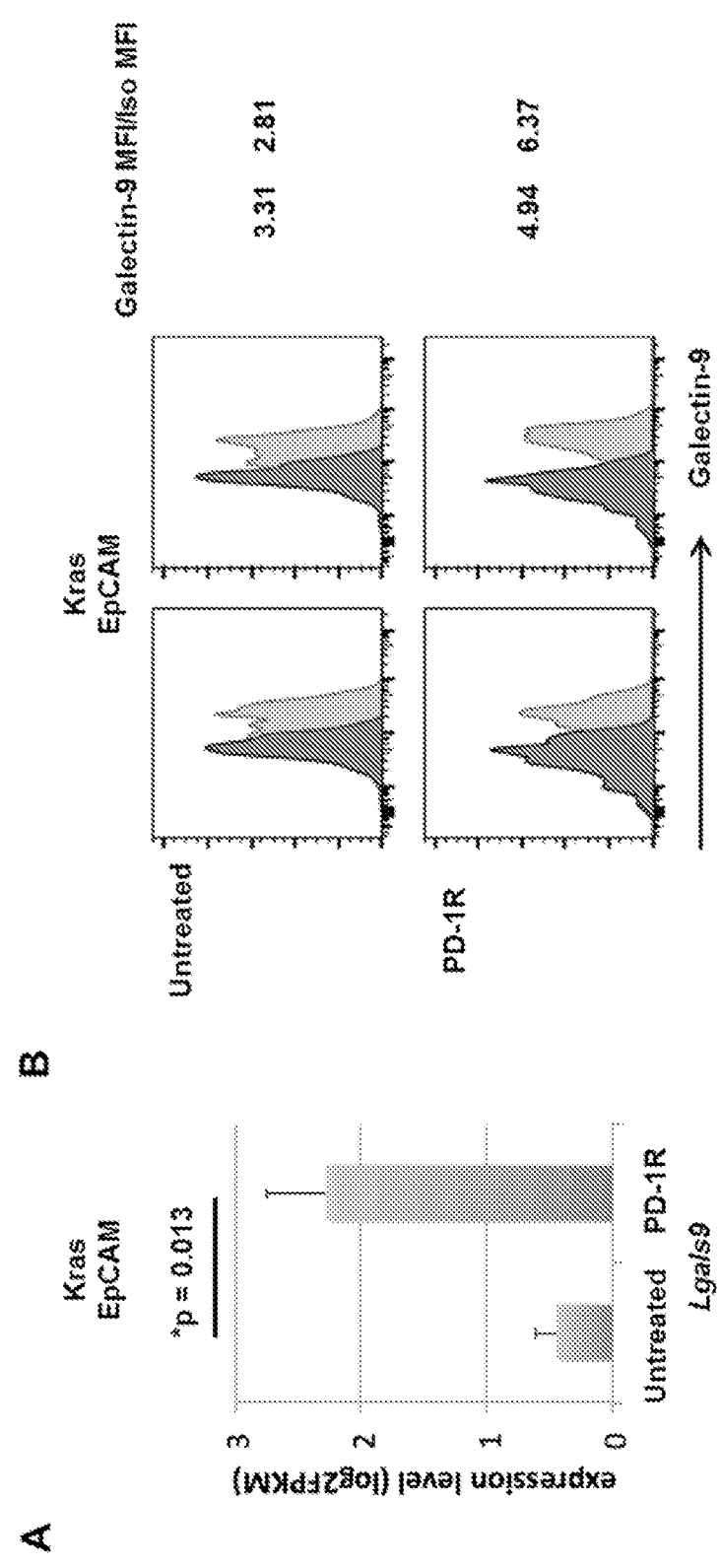

FIG. 9: Upregulation of Galectin-9 in PD-1 resistant Kras tumors

A) RNAseq analysis of CD45$^-$EpCAM$^+$ tumor cells from PD-1 naïve or PD-1 resistant tumors showing Lgals9 (Galectin-9). N=3 for both groups. B) Representative flow cytometry data of Galectin-9 expression from two untreated Kras tumors and two anti-PD-1 resistant tumors.

Figure 10:
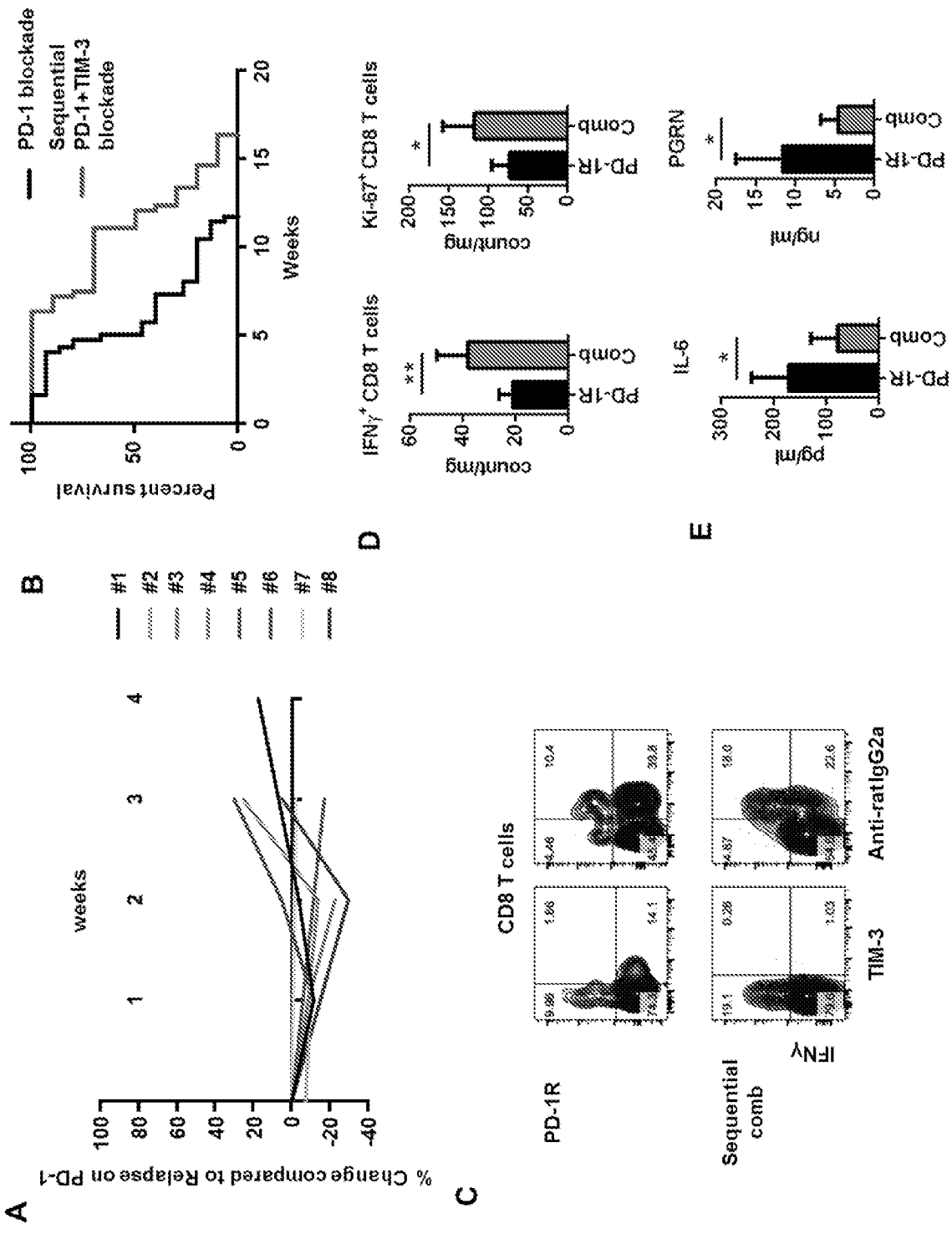

FIG. 10: Sequential anti-TIM-3 blocking displays clinical efficacy in anti-PD-1 adaptive resistant tumors A) Lung tumor measurements after TIM3 blockade treatment is included in the treatment. B) Survival after PD-1 blockade alone (anti-PD-1 resistant) or PD-1 and sequential TIM-3 blockade combination treatment (PD-1 alone: n=15 and sequential combination treatment: n=10) (P=0.0013) after documented tumor burden. Treatment started at week 0. Median survival PD1 5 weeks vs PD-1+TIM-3 sequential treatment 11.5 weeks. C) Representative flow cytometry data of IFN-gamma expression in CD8 T cells from anti-PD-1 resistant (PD-1R) and sequential anti-PD-1 plus anti-TIM-3 combination (Sequential comb): 2 weeks' anti-PD-1 and anti-TIM-3 combination treatment after development of resistance to PD-1 single treatment. Fluorescent conjugated anti-TIM-3 antibody is the same clone (RMT3-23) as the therapeutic antibody. Anti-rat IgG2a indicates binding of the therapeutic antibodies including anti-PD-1 and anti-TIM-3 antibodies. D) IFN-gamma and Ki-67 positive CD8 T cell counts from anti-PD-1 resistant (PD-1R) (n=6) and sequential anti-PD-1 plus anti-TIM-3 combination (comb) (n=6) (*P<0.05, **P<0.01). E) IL-6 and PGRN production in BALFs from PD-1R (n=6) and comb (n=6) (*P<0.05).

Figure 11:
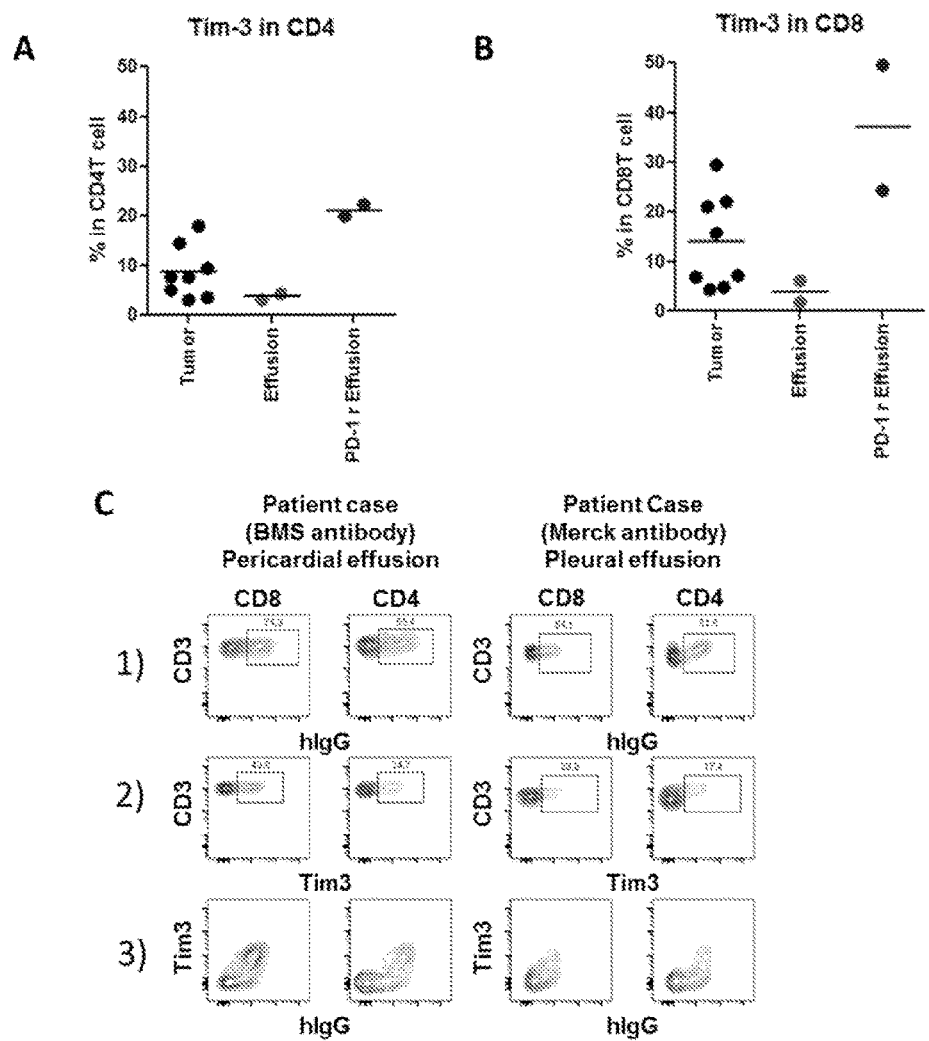

FIG. 11: Analysis of patient tumor and effusion samples Tim3 positive cells in freshly resected tumors or effusion samples from lung cancer patients who have not received treatment (tumor, effusion) or who have been treated with PD-1 blocking antibodies, initially responded to the treatment but subsequently developed acquired resistance (PD-1 r): A) CD4 T cells and B) CD8 T cells. C) Detailed analysis of effusion samples from patients who developed acquired resistance to PD-1 blockade. Graph 1) therapeutic antibody (hIgG) bound population among the CD8 and CD4 T cells. 2) A higher percentage of CD8 T cells express Tim3 as compared to CD4 T cells. 3) Most of the Tim3 expressing T cells have therapeutic antibody (hIgG) bound on their surface.

Figure 12:
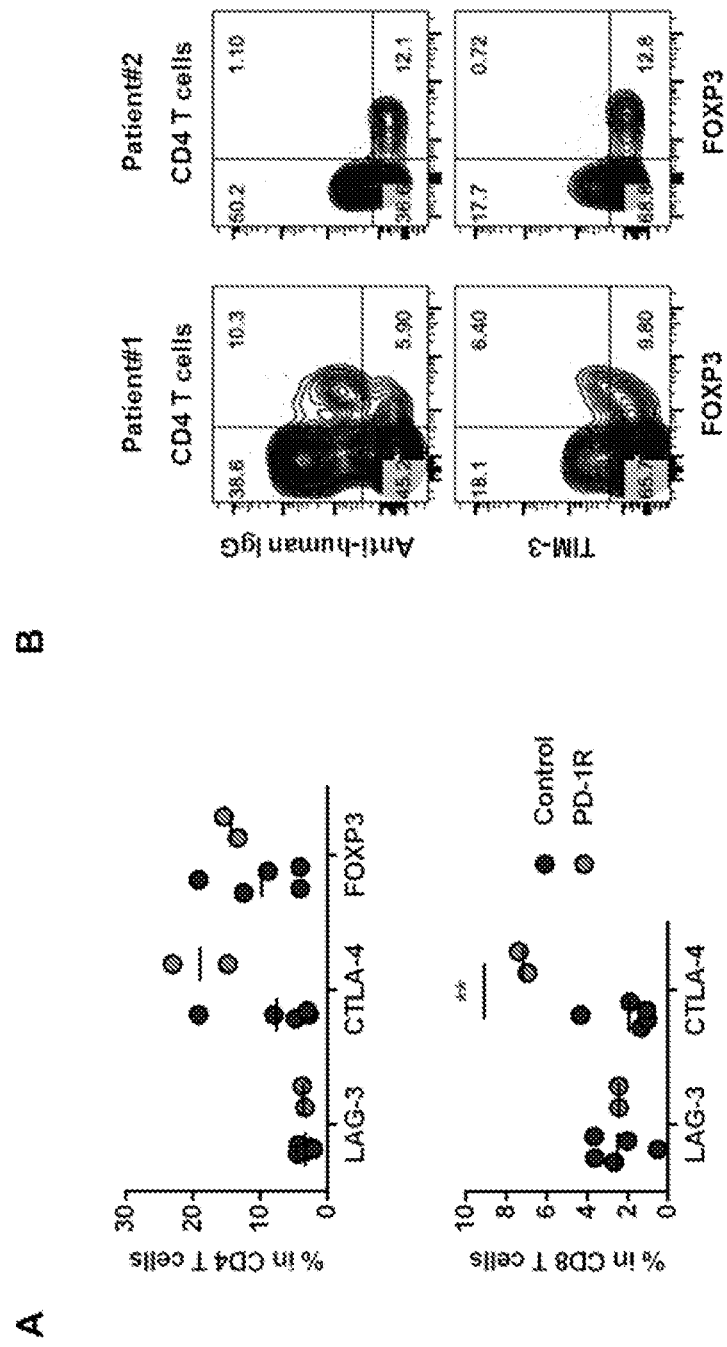

FIG. 12: Expression of checkpoint receptors in effusion samples.

A) Inhibitory T cell markers in CD4 and CD8 T cells from human effusion samples. Expression of LAG-3, CTLA-4, and FOXP3 was compared between control effusions from untreated patients (n=5) and two effusion samples from patients whose tumor developed resistance to anti-PD-1 treatment (PD-1R). ** P=0.0041. B) Therapeutic anti-PD-1 antibody binding and TIM-3 expression in regulatory T cells. In the effusion sample from Patient #1, 63.5% or 39.5% of FOXP3$^+$CD4 T cells show therapeutic antibody binding and TIM-3 expression. In the effusion sample from Patient #2, less than 10% of FOXP3$^+$CD4 T cells show anti-PD-1 antibody binding and TIM-3 positivity.

Figure 13:
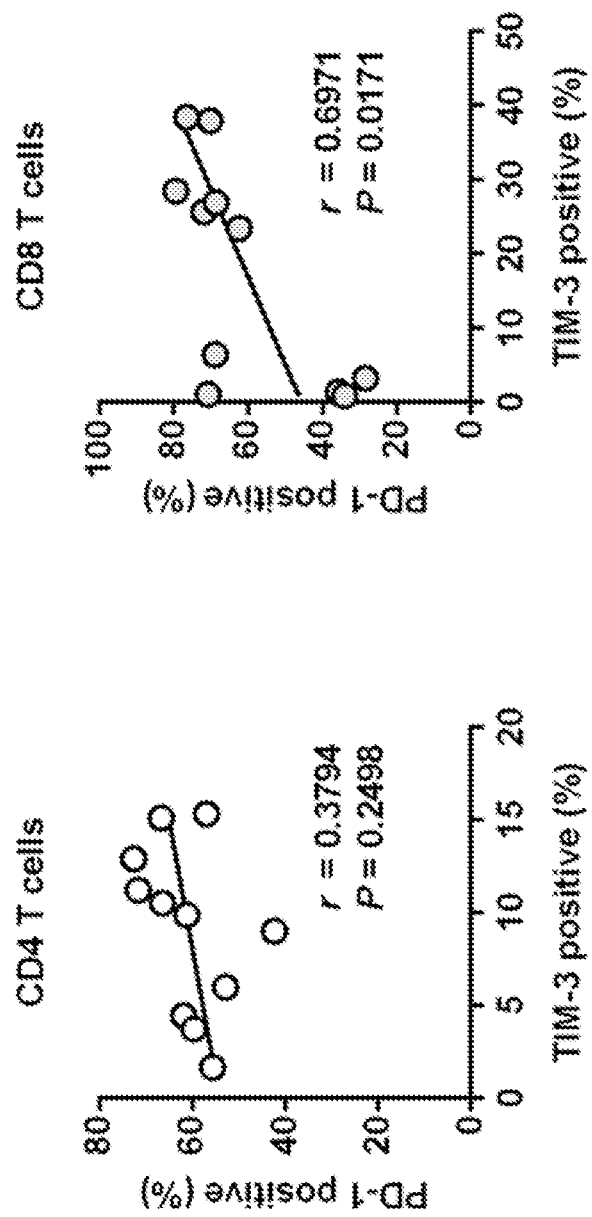

FIG. 13: Correlation between PD-1 and TIM-3 expression in CD4 and CD8 T cells from surgically resected tumor samples. The expression of PD-1 and TIM-3 was evaluated in CD4 and CD8 T cells from surgically resected non-small cell lung tumor tissues (n=11). A positive correlation between PD-1 and TIM-3 was detected in CD8 T cells but not CD4 T cells.

Figure 14:
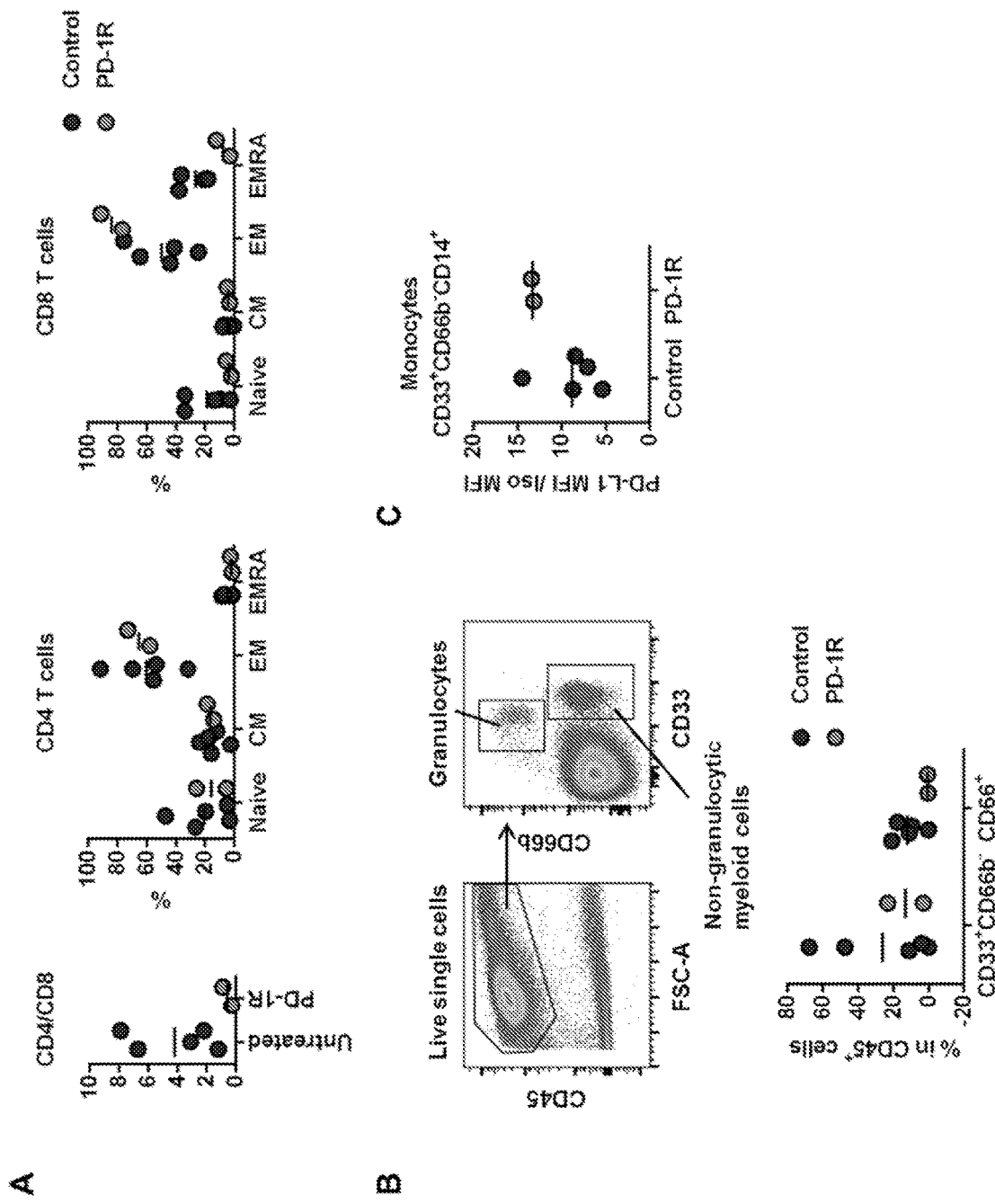

FIG. 14: Characteristics of T cells in patient effusion samples.

A) Left: CD4/CD8 ratio in anti-PD-1 resistant samples (PD-1R) compared to control. Mean of CD4/CD8 ratio in effusions: Control (Con) vs anti-PD-1 resistant (PD-1R)=4.231 vs 0.605 (P=0.1594). Right: ratio of each T cell subset in CD4 and CD8 T cells in effusions from two PD-1R patients compared to control (n=5). T cells were classified into naive: CD45RA$^+$CCR7$^+$, central memory (CM): CCR7$^+$CD45RA$^+$, effector memory (EM): CCR7$^+$CD45RA$^+$, effector memory re-expressing RA (EMRA): CCR7$^+$CD45RA$^+$. Mean of EM CD8 T cells: Control vs PD-1R=50.12% vs 84.10%. B and C Characteristics of myeloid cells in patient effusion samples. No significant change was detected in major myeloid cell populations; granulocytes (CD66b$^+$) and non-granulocytic myeloid cells (CD33$^+$CD66b$^-$) between untreated vs PD-1R samples (B). PD-L1 expression was evaluated in monocytes (CD33$^+$ CD66b$^-$CD14$^+$ cells). Mean of fold increase in PD-L1 MFI (effusion: untreated vs PD-1R=8.849 vs 13.33 (C).

Figure 15:
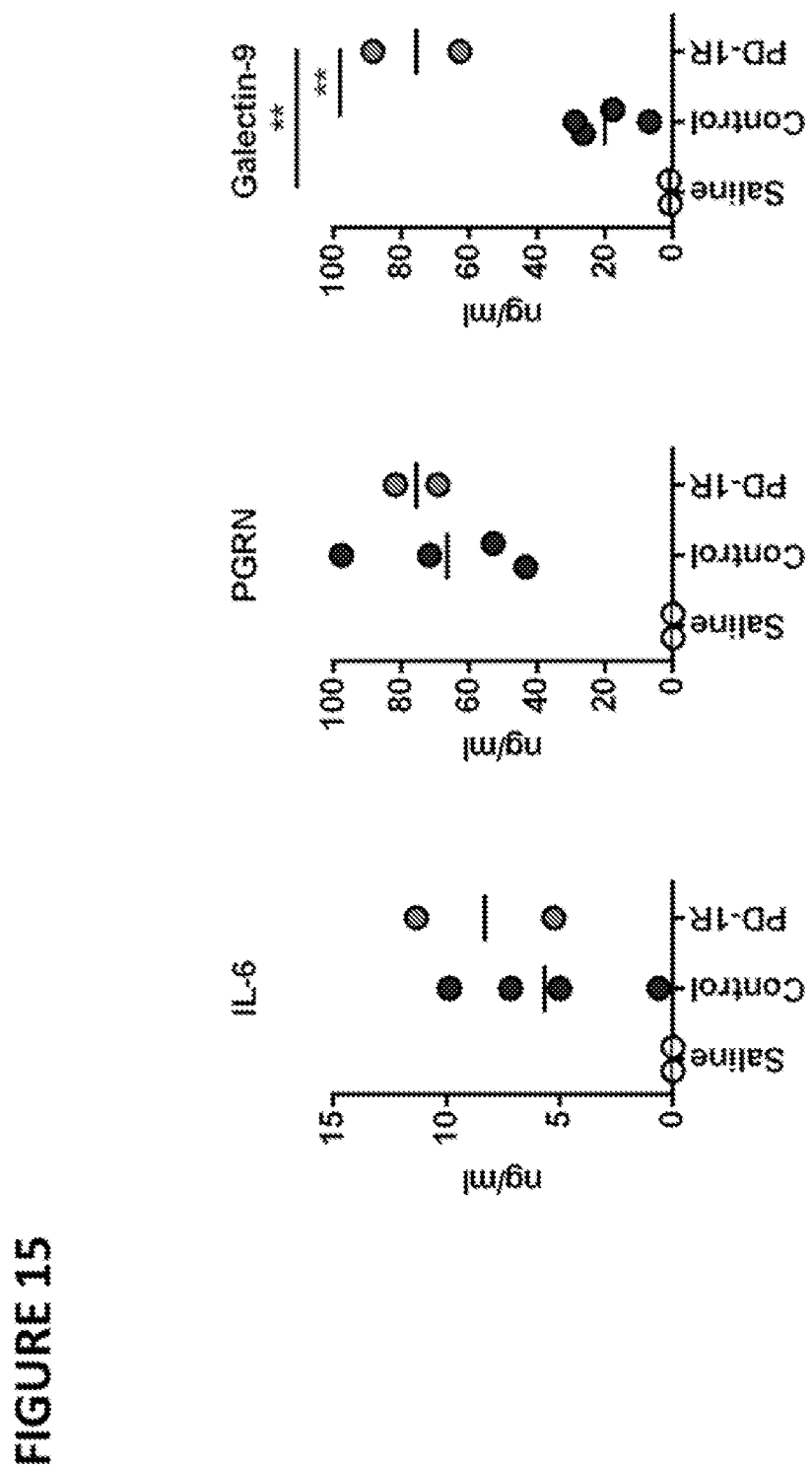

FIG. 15: Levels of proinflammatory cytokines and galectin-9 in patient effusion samples.

IL-6, PGRN and Galectin-9 concentrations in supernatants from effusion samples (Saline vs PD-1R; P=0.0027 and Control vs PD-1R: P=0.0052).

DETAILED DESCRIPTION OF THE INVENTION

The invention is based in part upon the surprising discovery that T cell immunoglobulin and mucin protein 3 (Tim3) is upregulated upon long term exposure to therapeutic anti-PD-1 antibody treatment at the time of relapse. PD-1 and PDL-1 immunotherapy has shown great success in the clinic in terms of the durability of the response. However, only a subset of patients responds to these treatments and some patients develop resistance to these treatments over time. The observation that Tim3 is overexpressed in patients receiving PD-1 and PDL-1 immunotherapy compared to immunotherapy naïve patients suggests that Tim3 blockade may overcome PD-1 and PDL-1 immunotherapy resistance.

Tim3 Inhibitors

A T cell immunoglobulin and mucin protein 3 (Tim3) inhibitor is a compound that decreases expression or activity of Tim3. TIM-3 is a member of the T-cell Immunoglobulin- and Mucin-domain-containing family of type I membrane glycoproteins that regulate autoimmune and allergic disease. TIM-3 is selectively expressed on Th1 cells and interacts with galectin-9. It negatively regulates Th1 responses and affects macrophage activation. The 280 amino acid mature human TIM-3 contains a V-type Ig-like domain that shows multiple polymorphisms, followed by a mucin-like domain in the 171 amino acid extracellular region. One splice variant of TIM-3 is truncated within the mucin domain and presumably is secreted.

A Tim3 inhibitor decreases expression or activity of Tim3. A decrease in Tim3 activity is defined by a reduction of a biological function of the Tim3. For example, a decrease or reduction in Tim3 expression or biological activity refers to at least a 1%, 2%, 5%, 10%, 15%, 20%, 25%, 30%, 35%, 40%, 45%, 50%, 60%, 70%, 80%, 90% or 100% decrease in Tim3 expression or activity compared to a control. For example, the control is the expression or activity of tTim3 before treatment or in a subject that has not received any treatment.

Tim3 expression is measured by detecting a Tim3 transcript or protein using standard methods known in the art, such as RT-PCR, microarray, and immunoblotting or immunohistochemistry with Tim3-specific antibodies. For example, a decrease in Tim3 expression refers to at least a 1%, 2%, 5%, 10%, 15%, 20%, 25%, 30%, 35%, 40%, 45%, 50%, 60%, 70%, 80%, 90% or 100% decrease in the level of Tim3 mRNA or VRK protein.

The Tim3 inhibitor is an antibody or fragment thereof specific to Tim3. Methods for designing and producing specific antibodies are well-known in the art. In particular embodiments the Tim3 inhibitor is a bi-specific antibody. For example, the bi-specific antibody is specific for Tim3 and PD-1 or PDL-1.

The Tim3 inhibitor can also be a small molecule. A "small molecule" as used herein, is meant to refer to a composition that has a molecular weight in the range of less than about 5 kD to 50 daltons, for example less than about 4 kD, less than about 3.5 kD, less than about 3 kD, less than about 2.5 kD, less than about 2 kD, less than about 1.5 kD, less than about 1 kD, less than 750 daltons, less than 500 daltons, less than about 450 daltons, less than about 400 daltons, less than about 350 daltons, less than about 300 daltons, less than 250 daltons, less than about 200 daltons, less than about 150 daltons, less than about 100 daltons. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Alternatively, the Tim3 inhibitor is for example an antisense Tim3 nucleic acid, a Tim3 specific short-interfering RNA, or a Tim3-specific ribozyme. By the term "siRNA" is meant a double stranded RNA molecule which prevents translation of a target mRNA. Standard techniques of introducing siRNA into a cell are used, including those in which DNA is a template from which an siRNA is transcribed. The siRNA includes a sense Tim3 nucleic acid sequence, an anti-sense Tim3nucleic acid sequence or both. Optionally, the siRNA is constructed such that a single transcript has both the sense and complementary antisense sequences from the target gene, e.g., a hairpin (shRNA). Examples of siRNAs and shRNAs are disclosed in the examples herein.

Binding of the siRNA to a Tim3 transcript in the target cell results in a reduction in Tim3 production by the cell. The length of the oligonucleotide is at least 10 nucleotides and may be as long as the naturally-occurring Tim3 transcript. Preferably, the oligonucleotide is 19-25 nucleotides in length. Most preferably, the oligonucleotide is less than 75, 50, 25 nucleotides in length.

Therapeutic Methods

In various aspects the invention provides method of treating or preventing PD-1 or PDL-1 resistance in a subject. The method includes administering to the subject a compound that inhibits the expression or activity of a T cell immunoglobulin and mucin protein 3 (Tim3).

Cells are directly contacted with the compound. Alternatively, the compound is administered systemically.

The subject has or is receiving PD-1 or PDL-1 therapy such as PD-1 or PDL-1 immunotherapy.

The methods described herein are useful to alleviate the symptoms of a variety of cancers. Any cancer exhibiting PD-1 or PDL-1 resistance is suitable for treatment with the methods of the invention.

Treatment is efficacious if the treatment leads to clinical benefit such as, a decrease in size, prevalence, or metastatic potential of the tumor in the subject. When treatment is applied prophylactically, "efficacious" means that the treatment retards or prevents tumors from forming or prevents or alleviates a symptom of clinical symptom of the tumor.

Efficaciousness is determined in association with any known method for diagnosing or treating the particular tumor type.

Therapeutic Administration

The invention includes administering to a subject composition comprising a Tim3 inhibitor.

An effective amount of a therapeutic compound is preferably from about 0.1 mg/kg to about 150 mg/kg. Effective doses vary, as recognized by those skilled in the art, depending on route of administration, excipient usage, and coadministration with other therapeutic treatments including use of other anti-proliferative agents or therapeutic agents for treating, preventing or alleviating a symptom of a cancer. A therapeutic regimen is carried out by identifying a mammal, e.g., a human patient suffering from a cancer using standard methods.

Doses may be administered once, or more than once. In some embodiments, it is preferred that the therapeutic compound is administered once a week, twice a week, three times a week, four times a week, five times a week, six times a week, or seven times a week for a predetermined duration of time. The predetermined duration of time may be 1 week, 2 weeks, 3 weeks, 4 weeks, 5 weeks, 6 weeks, 7 weeks, 2 months, 3 months, 4 months, 5 months, 6 months, 7 months, 8 months, 9 months, 10 months, 11 months, or up to 1 year.

The pharmaceutical compound is administered to such an individual using methods known in the art. Preferably, the compound is administered orally, rectally, nasally, topically or parenterally, e.g., subcutaneously, intraperitoneally, intramuscularly, and intravenously. The inhibitors are optionally formulated as a component of a cocktail of therapeutic drugs to treat cancers. Examples of formulations suitable for parenteral administration include aqueous solutions of the active agent in an isotonic saline solution, a 5% glucose solution, or another standard pharmaceutically acceptable excipient. Standard solubilizing agents such as PVP or cyclodextrins are also utilized as pharmaceutical excipients for delivery of the therapeutic compounds.

The therapeutic compounds described herein are formulated into compositions for other routes of administration utilizing conventional methods. For example, the therapeutic compounds are formulated in a capsule or a tablet for oral administration. Capsules may contain any standard pharmaceutically acceptable materials such as gelatin or cellulose. Tablets may be formulated in accordance with conventional procedures by compressing mixtures of a therapeutic compound with a solid carrier and a lubricant. Examples of solid carriers include starch and sugar bentonite. The compound is administered in the form of a hard shell tablet or a capsule containing a binder, e.g., lactose or mannitol, conventional filler, and a tableting agent. Other formulations include an ointment, suppository, paste, spray, patch, cream, gel, resorbable sponge, or foam. Such formulations are produced using methods well known in the art.

Therapeutic compounds are effective upon direct contact of the compound with the affected tissue. Accordingly, the compound is administered topically. Alternatively, the therapeutic compounds are administered systemically. For example, the compounds are administered by inhalation. The compounds are delivered in the form of an aerosol spray from pressured container or dispenser which contains a suitable propellant, e.g., a gas such as carbon dioxide, or a nebulizer.

Additionally, compounds are administered by implanting (either directly into an organ or subcutaneously) a solid or resorbable matrix which slowly releases the compound into adjacent and surrounding tissues of the subject.

In some embodiments, it is preferred that the therapeutic compounds described herein are administered in combination with another therapeutic agent, such as a chemotherapeutic agent, radiation therapy, or an anti-mitotic agent. In some aspects, the anti-mitotic agent is administered prior to administration of the present therapeutic compound, in order to induce additional chromosomal instability to increase the efficacy of the present invention to targeting cancer cells. Examples of anti-mitotic agents include taxanes (i.e., paclitaxel, docetaxel), and vinca alkaloids (i.e., vinblastine, vincristine, vindesine, vinorelbine).

Screening Assays

The invention also provides a method of identifying subjects that have developed resistance to PD-1 or PDL-1 therapy, such as PD-1 or PDL-1 immunotherapy. I A method includes detecting the expression level of Tim3 in a subject sample, wherein an increase of expression of Tim3 compared to a normal control cell indicates that the subject has PD-1 or PDL-1 resistance.

The invention further includes methods of selecting a subject whom would derive a benefit from PD-1 or PDL-1 therapy by detecting the expression level of Tim3 in a subject sample. A similarity of expression of Tim3 compared to a normal control cell indicates that the subject would derive a benefit from PD-1 or PDL-1 therapy.

Definitions

The term "polypeptide" refers, in one embodiment, to a protein or, in another embodiment, to protein fragment or fragments or, in another embodiment, a string of amino acids. In one embodiment, reference to "peptide" or "polypeptide" when in reference to any polypeptide of this invention, is meant to include native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into cells. Such modifications include, but are not limited to N terminal, C terminal or peptide bond modification, including, but not limited to, backbone modifications, and residue modification, each of which represents an additional embodiment of the invention. Methods for preparing peptidomimetic compounds are well known in the art and are specified, for example, in Quantitative Drug Design, C. A. Ramsden Gd., Chapter 17.2, F. Choplin Pergamon Press (1992).

As used interchangeably herein, the terms "oligonucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The term "homology", when in reference to any nucleic acid sequence indicates a percentage of nucleotides in a candidate sequence that are identical with the nucleotides of a corresponding native nucleic acid sequence. Homology may be determined by computer algorithm for sequence alignment, by methods well described in the art. For example, computer algorithm analysis of nucleic acid or amino acid sequence homology may include the utilization of any number of software packages available, such as, for example, the BLAST, DOMAIN, BEAUTY (BLAST Enhanced Alignment Utility), GENPEPT and TREMBL packages.

As used herein, the term "substantial sequence identity" or "substantial homology" is used to indicate that a sequence exhibits substantial structural or functional equivalence with another sequence. Any structural or functional differences between sequences having substantial sequence identity or substantial homology will be de minimus; that is, they will not affect the ability of the sequence to function as indicated in the desired application. Differences may be due to inherent variations in codon usage among different species, for example. Structural differences are considered de minimus if there is a significant amount of sequence overlap or similarity between two or more different sequences or if the different sequences exhibit similar physical characteristics even if the sequences differ in length or structure. Such characteristics include, for example, the ability to hybridize under defined conditions, or in the case of proteins, immunological crossreactivity, similar enzymatic activity, etc. The skilled practitioner can readily determine each of these characteristics by art known methods.

Additionally, two nucleotide sequences are "substantially complementary" if the sequences have at least about 70 percent or greater, more preferably 80 percent or greater, even more preferably about 90 percent or greater, and most preferably about 95 percent or greater sequence similarity between them. Two amino acid sequences are substantially homologous if they have at least 50%, preferably at least 70%, more preferably at least 80%, even more preferably at least 90%, and most preferably at least 95% similarity between the active, or functionally relevant, portions of the polypeptides.

To determine the percent identity of two sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

Thus, treating may include suppressing, inhibiting, preventing, treating, or a combination thereof. Treating refers inter alia to increasing time to sustained progression, expediting remission, inducing remission, augmenting remission, speeding recovery, increasing efficacy of or decreasing resistance to alternative therapeutics, or a combination thereof "Suppressing" or "inhibiting", refers inter alia to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. The symptoms are primary, while in another embodiment, symptoms are secondary. "Primary" refers to a symptom that is a direct result of the proliferative disorder, while, secondary refers to a symptom that is derived from or consequent to a primary cause. Symptoms may be any manifestation of a disease or pathological condition.

The "treatment of cancer or tumor cells", refers to an amount of peptide or nucleic acid, described throughout the specification, capable of invoking one or more of the following effects: (1) inhibition of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "an ameliorated symptom" or "treated symptom" refers to a symptom which approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer to shrink rr or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "cancer" refers to all types of cancer or neoplasm or malignant tumors found in mammals, including, but not limited to: melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, uterus and Medulloblastoma.

A "proliferative disorder" is a disease or condition caused by cells which grow more quickly than normal cells, i.e., tumor cells. Proliferative disorders include benign tumors and malignant tumors. When classified by structure of the tumor, proliferative disorders include solid tumors and hematopoietic tumors.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

By the term "modulate," it is meant that any of the mentioned activities, are, e.g., increased, enhanced, increased, augmented, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

As used herein, the term "administering to a cell" (e.g., an expression vector, nucleic acid, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

EXAMPLES

Example 1: Mouse Husbandry and Breeding

EGFR transgenic mice carrying tetracycline inducible human EGFR cDNA were previously generated (1), crossed with CC10-RTTA mice expressing reverse tetracycline activator from lung Clara cell CC10 promoter, and maintained in mixed background. Double positive (EGFR and CC10 RTTA) progeny were fed with doxycycline diet starting at 5-6 weeks of age for the induction of tumors and maintained on doxycyline throughout the study. Mice were euthanatized when they reached tumor burden euthanasia criteria. All breedings and in vivo experiments were performed with the approval of the DFCI Animal Care and Use Committee.

Example 2: Mouse Treatment Studies

EGFR transgenic mice carrying tetracycline inducible human EGFR cDNA were previously generated (1), crossed with CC10-RTTA mice expressing reverse tetracycline activator from the lung Clara cell CC10 promoter, and maintained in mixed background. Double positive (EGFR and CC10 RTTA) progeny were fed with a doxycycline diet starting at 5-6 weeks of age for the induction of tumors and maintained on doxycycline throughout the study. Kras G12D mice were given adenovirus expressing Cre recombinase ($5 \times 10^6$ titer) intranasally at 5 weeks of age for induction of recombination and tumor formation. All mice were maintained on a mixed (C57Bl/6, FVB, and S129) background. Mice were euthanized when they reached tumor burden euthanasia criteria determined by health condition as evaluated by veterinary technicians upon twice daily health checks. TIM-3 antibody was added to the treatment regimen when mice displayed clinical signs of progressive disease which was confirmed by MRI. All breedings and in vivo experiments were performed with the approval of the DFCI Animal Care and Use Committee. MRI imaging and evaluation of tumor size were performed as described previously (2). PD-1 blocking antibody (clone 29F.1A12), TIM-3 blocking antibody (clone RMT3-23: Bio X cell) and their isotype controls (clone 2A3: Bio X cell) were injected intraperitoneally into mice for therapeutic treatment (3 times a week, 200 μg for PD1 and 100 μg for TIM-3 per dose).

Patient Sample Collection

Anonomized patient samples were obtained under IRB approved protocols DFCI 02-180, 11-104 and BIDMC 2001-P-001089. Biopsies and effusions were obtained during routine clinical procedures.

Immune Analysis for Patient and Mouse Samples

Murine tumor and immune cell characterization was performed as previously described (2). The processing for freshly resected patient lung tumor samples was performed similarly. For freshly collected effusion samples, the cells were treated with RBC lysis after spin and directly used for staining after cell screening (70 µm). Isolated cells were stained with LIVE/DEAD fixable dead cell stain kit (invitrogen) before surface marker staining. The antibodies used for immune analysis are listed in the Table 1. For counting absolute numbers of immune cell populations, AccuCheck Counting Beads (Molecular probes) were used according to the manufacturer's protocol. For detecting anti PD-1 antibody binding, Rabbit anti human IgG/Rabbit isotype control IgG (SouthernBiotech) and secondary Goat anti Rabbit IgG (SouthernBiotech) for human and anti Rat IgG2a (r2a-21B2: eBioscience) for mice were used without prior Fc blocking (Miltenyi Biotech and BD Biosciences) which was used for all the other staining. For intracellular cytokine staining, total tumor bearing lung cells were fractionated over cell separation media as previously described (2). Isolated mononuclear cells were stimulated with 50 ng/ml PMA (Sigma) and 500 ng/ml Ionomycin (Sigma) for 4 h in the presence of Golgi plug (BD Biosciences). Fixation/permeabilization buffers (eBioscience) or BD Cytofix/Cytoperm buffers (BD Biosciences) were used for both mice and human samples for intracellular staining. Acquisition of eight color samples was performed on a BD Canto II cytometer equipped with Diva software and analyzed using Flowjo.

Tumor Infiltrating T Cell Sorting and RNA Sequencing

Sorting of tumor infiltrating T cells (CD45$^+$TCRb$^+$CD11b$^-$CD11c$^-$CD19$^-$DX5$^-$ TER119$^-$Ly6G$^-$) and tumor cells (enriched epithelial cell population: CD45$^-$EpCAM$^+$ was utilized as tumor cells) was performed on a BD FACSAria II cell sorter. The gating method for sorting is shown in Supplementary Methods. RNA was prepared from sorted lymphocyte populations using the Arcturus PicoPure kit (Life Technologies) and RNA quantified using Ribo-Green (Life Technologies) per the manufacturer's protocol. 10 ng of total RNA was used for library preparation using the Nugen Ovation system (Nugen) per the manufacturer's instructions. Libraries were quantitated and analyzed using a high sensitivity DNA chip assay (Agilent) and by quantitative PCR. Pooled libraries were sequenced on an Illumina HiSeq instrument to a minimum read depth of 30 million reads. RNA-seq reads were aligned to the mm9 Ensembl transcript annotation (release 65) using the PRADA pipeline (10.1093/bioinformatics/btu169), and FPKM expression values were determined using Cufflinks with mm9 RefSeq gene annotations. FPKM values were determined using Cufflinks, log 2-transformed and then used to calculate fold-change (where a fold change over 1.5 denoted overexpressed and less than −1.5 denoted underexpressed) and Benjamini and Hochberg adjusted p-values (or q-values). For heatmaps, the log 2-transformed FPKM values were colored on a black-red scale ranging from 0 to 6, and the fold-changes of each resistant tumor compared to its genotype-matched untreated tumors were colored on blue-red scale ranging from 0 to 6.

Measurement of Soluble Factor Concentrations in BALFs from Mice and Supernatants of Effusions from Lung Cancer Patients Broncho alveolar lavage fluid (BALF) collection was performed as described previously (2). Collected BALFs and supernatants of effusions were kept at −80° before performing the ELISA. Cytokine and chemokines were measured with ELISA kits according to the manufacturer's protocol; mouse and human IL-6 (BD biosciences), GRN (R&D Systems) and human Galectin-9 (R&D Systems).

Statistical Analysis

All numerical data are shown as mean±SD. Data were analyzed using two-tailed unpaired Student's t test for comparisons of two groups and one-way ANOVA with Tukey post-test for three groups. Correlation was evaluated using Pearson's correlation coefficient. P values for the survival curves have been calculated using a log rank test.

Immune Cell Analysis

Total mouse lung cell and tumor infiltrating immune cell characterization was performed as previously described (2). Freshly resected patient tumor samples were processed similarly.

Isolated cells were stained with antibodies (see Table 1) after Fc blocking (Miltenyi Biotec). For evaluating PD-1 antibody binding, cells were incubated with rabbit isotype control or rabbit anti human IgG antibody (Southern Biotech) and then stained with fluorescent conjugated Goat anti Rabbit antibody (Southern Biotech). Flowcytometry and data analysis were performed similarly to mouse samples (2). Freshly collected effusion samples treated with RBC lysis and stained by the same protocol with tumor samples. Anonymized patient samples were obtained under IRB approved protocols 02-180 and 11-104 as part of patient's normal clinical procedure and not and additional procedure.

TABLE 1

| Antibody list used for patient samples: | | |
|---|---|---|
| CD3 | UCHT1 | BD Biosciences |
| CD4 | RPA-T4 | Biolegend |
| CD8a | RPA-T8 | BD Biosciences |
| Tim-3 | F38-2E2 | Biolegend |

REFERENCES

1. Li D, Shimamura T, Ji H, Chen L, Haringsma H J, McNamara K, et al. Bronchial and peripheral murine lung carcinomas induced by T790M-L858R mutant EGFR respond to HKI-272 and rapamycin combination therapy. Cancer Cell. 2007; 12:81-93.
2. Akbay E A, Koyama S, Carretero J, Altabef A, Tchaicha J H, Christensen C L, et al. Activation of the PD-1 pathway contributes to immune escape in EGFR-driven lung tumors. Cancer Discov. 2013; 3:1355-63.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

I claim:

1. A method of treating a subject with a cancer that has acquired resistance to a PD-1 or PDL-1 immunotherapy, comprising administering to said subject an antibody that inhibits the expression or activity of a T cell immunoglobulin and mucin protein 3 (Tim3) and a PD-1 or PDL-1 immunotherapy.

2. The method of claim 1, wherein the cancer is a KRAS or EGFR mutant cancer.

3. The method of claim 2, wherein the cancer has a EGFR T790M L858R mutation.

4. The method of claim 1, wherein said cancer is a lung cancer, melanoma, kidney cancer, a head and neck cancer, bladder cancer or an upper gastrointestinal cancer.

5. The method of claim 4, wherein the kidney cancer is a renal cell cancer.

6. The method of claim 4, wherein the lung cancer is a non-small-cell lung cancer.

7. The method of claim 1, wherein the antibody that inhibits the expression or activity of Tim3 is bi-specific.

8. The method of claim 1, wherein the PD-1 or PDL-1 immunotherapy is administered concurrently or sequentially with the antibody that inhibits the expression or activity of Tim3.

9. The method of claim 1, further comprising administering a chemotherapeutic agent or radiation therapy.

10. The method of claim 9, wherein the chemotherapeutic agent is a targeted therapy.

11. The method of claim 9, wherein the chemotherapeutic agent is an EGFR tyrosine kinase inhibitor.

12. The method of claim 11, wherein the EGFR tyrosine kinase inhibitor is WZ4002.

13. A method of deriving a clinical benefit from a PD-1 or PDL-1 immunotherapy in a subject with a cancer that has acquired resistance to PD-1 or PDL-1 immunotherapy, comprising administering to said subject an antibody that inhibits the expression or activity of a T cell immunoglobulin and mucin protein 3 (Tim3) and a PD-1 or PDL-1 immunotherapy.

* * * * *